(12) United States Patent  
Wallace et al.

(10) Patent No.: US 9,218,734 B2
(45) Date of Patent: Dec. 22, 2015

(54) SYSTEM AND METHOD FOR DETECTING HAND HYGIENE COMPLIANCE

(71) Applicant: GENERAL ELECTRIC COMPANY, Schenectady, NY (US)

(72) Inventors: Robert Lee Wallace, Glen Allen, VA (US); Todd Franklin Scarola, Crozier, VA (US)

(73) Assignee: General Electric Company, Schenectady, NY (US)

( * ) Notice: Subject to any disclaimer, the term of this patent is extended or adjusted under 35 U.S.C. 154(b) by 63 days.

(21) Appl. No.: 14/140,067

(22) Filed: Dec. 24, 2013

(65) Prior Publication Data

US 2015/0179047 A1  Jun. 25, 2015

(51) Int. Cl.
*G08B 23/00*  (2006.01)
*G08B 21/24*  (2006.01)

(52) U.S. Cl.
CPC ................... *G08B 21/245* (2013.01)

(58) Field of Classification Search
CPC .................................................. G08B 21/245
USPC ........ 340/573.1, 539.1, 561, 691.1, 692, 540, 340/541
See application file for complete search history.

(56) References Cited

U.S. PATENT DOCUMENTS

| | | | |
|---|---|---|---|
| 6,727,818 B1 * | 4/2004 | Wildman et al. | 340/573.1 |
| 8,648,724 B2 * | 2/2014 | Forsberg et al. | 340/573.1 |
| 8,816,860 B2 * | 8/2014 | Ophardt et al. | 340/573.1 |
| 2011/0234598 A1 * | 9/2011 | Scarola et al. | 345/440.1 |

\* cited by examiner

*Primary Examiner* — Tai T Nguyen

(57) ABSTRACT

A device configured to be disposed on or proximate to a dispenser and to detect hand hygiene compliance is provided. The device includes a proximity detection device configured to detect a location and an identifier of a caregiver within a proximity of the device. The device also includes a transducer configured to detect a release event from the dispenser by detecting an acoustic waveform emitted from the dispenser when soap or sanitizer is released from the dispenser. The device further includes a processing device configured to associate the caregiver with the release event based on detecting the acoustic waveform when the caregiver is located within the proximity of the device.

20 Claims, 2 Drawing Sheets

SYSTEM AND METHOD FOR DETECTING HAND HYGIENE COMPLIANCE

BACKGROUND

The subject matter disclosed herein relates to a system for and method to detect hand hygiene compliance.

Infections can result in operation of hospitals or clinics or other healthcare environments in association with interaction of the healthcare provider with multiple patients, deliverables, or surfaces over a time interval or at the surgical point of care. Not only can infections be harmful to the health of the patient, but also increase costs to treat the patient and can harm a reputation of a healthcare institution. Typically, a healthcare institution includes rules or protocols for personnel to follow to promote hygiene. Systems are needed throughout the healthcare institution to monitor and to detect hygiene (e.g., hand hygiene) compliance.

BRIEF DESCRIPTION

In accordance with one embodiment, a device configured to be disposed on or proximate to a dispenser and to detect hand hygiene compliance is provided. The device includes a proximity detection device configured to detect a location and an identifier of a caregiver within a proximity of the device. The device also includes a transducer configured to detect a release event from the dispenser by detecting an acoustic waveform emitted from the dispenser when soap or sanitizer is released from the dispenser. The device further includes a processing device configured to associate the caregiver with the release event based on detecting the acoustic waveform when the caregiver is located within the proximity of the device.

In accordance with an additional embodiment, a method to detect hand hygiene compliance is provided. The method includes detecting, via a proximity detection device, a location and an identifier of a caregiver within a proximity of a dispenser. The method also includes detecting, via a transducer, a release event from the dispenser by detecting an acoustic waveform emitted from the dispenser when soap or sanitizer is released from the dispenser. The method further includes associating, via a processing device, the caregiver with the release event based on detecting the acoustic waveform when the caregiver is located within the proximity of the dispenser.

In accordance with a further embodiment, a device configured to be disposed on or proximate to a dispenser and to detect hand hygiene compliance is provided. The device includes a memory structure encoding one or more processor-executable routines, wherein the routines, when executed, cause acts be performed. The acts include receiving an identifier of a caregiver within a proximity of the device and receiving, from a transducer, a signal representative of a detected acoustic waveform emitted from the dispenser when soap or sanitizer is released from the dispenser during a release event. The acts also include comparing the detected acoustic waveform to at least one acoustic waveform stored on the memory structure to determine an occurrence of the release event, wherein the at least one acoustic waveform represents a specific type of dispenser. The acts further include associating the caregiver with the release event based on detecting the acoustic waveform when the caregiver is located within the proximity of the dispenser. The device also includes a processing component configured to access and execute the one or more routines encoded by the memory structure.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following embodiments as an example are generally described with reference to a healthcare environment. It can be appreciated that described embodiments may be utilized in many environments (e.g., home, food service, ambulatory or healthcare settings) and are not limited to the subject matter described herein.

Figure 1:
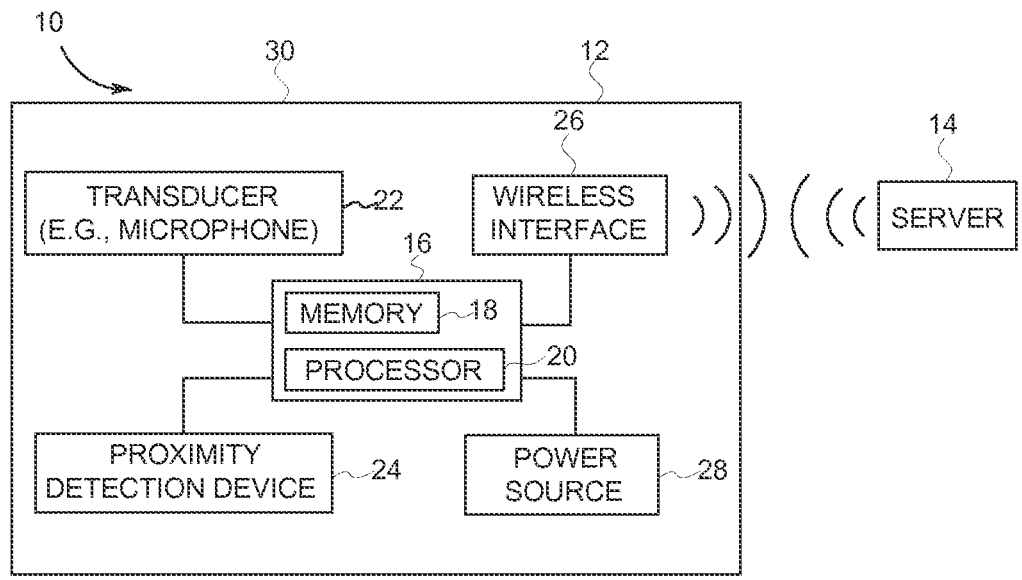
FIG. 1 depicts a block diagram of an embodiment of a system to manage hand hygiene having a device (e.g., hand hygiene detection device) coupled to a server.

FIG. 1 depicts a block diagram of an embodiment of a system 10 to manage hand hygiene having a device 12 (e.g., hand hygiene detection device) coupled to a server 14. In one embodiment, the system 10 may be directed to manage hand hygiene in association with a caregiver or individual (e.g., a visitor or healthcare personnel such as a doctor, nurse, etc.) in regard to delivery of healthcare (e.g., diagnosis or treatment) to a patient. The device 12 is configured to be disposed on (e.g., via adhesive) or proximate to a dispenser of soap or sanitizer (see FIG. 2). One or more of the devices 12 may be disposed throughout a healthcare facility. The device 12 is configured to detect hand hygiene compliance by detecting a release event from the dispenser (i.e., dispersal of soap or sanitizer) by detecting an acoustic waveform (i.e., audible sound or waveform) emitted from the dispenser when soap or sanitizer is released from the dispenser and associating a caregiver within proximity of the device 12 or the dispenser during the release event with the release event. The acoustic waveform is representative of an audible sound emitted by the dispenser. The acoustic waveform does not include radio frequency (RF) waveforms.

The device 12 may in one embodiment include a system on a chip 16 that include one or more each of a memory 18 and a processor 20. The system on a chip 16 is an integrated circuit that integrates components of a computer or electronic system on a single chip. For example, digital, analog, mixed-signal, and/or radio-frequency functions may be disposed all on a single chip substrate. Besides the memory 18 and the processor 20, the system on a chip 16 may include timing sources (e.g., oscillators, phase-locked loops), peripherals (counter-timers, real-time timers, power-on reset generators), external interfaces (e.g., USB, FireWire, Ethernet, USART, SPI, etc.), analog interfaces (e.g., digital-to-analog converters, analog-to-digital converters, etc.), and/or voltage regulators and power management circuits. Alternative to the system on a chip 16, the device 12 may include a system in package (i.e., multiple chips having the components described above in a single package) having one or more each of the memory 18 and the processor 20. The memory 18 may include a non-transitory computer-storage medium (e.g., compact disc (CD or magnetic storage medium), DVD, memory stick, random access memory (RAM), random operating memory (ROM), flash memory, EEPROM, etc.) configured to receive, record, and store data and/or instructions. The processor(s) 20 may execute the instructions stored on the memory 18. The processors(s) 20 may include one or more microprocessors, such as one or more "general-purpose" microprocessors, one or more special-purpose microprocessors and/or application specific integrated circuits (ASICS), or some combination thereof.

The depicted implementation of the device 12 also includes a transducer 22, proximity detection device 24, wireless interface 26, and a power source 28. In certain embodiments, one or more of the transducer 22, the proximity detection device 24, wireless interface 26, or power source 28 may be part of the system on a chip 16 (i.e., disposed on the single chip substrate). The transducer 22 may include a microphone configured to detect the release event from the dispenser by detecting an acoustic waveform emitted from the dispenser when soap or sanitizer is released from the dispenser. The processor 20 receives from the transducer 22 a signal representative of the detected acoustic waveform. Different types of dispensers (e.g., manual, automatic, brand, etc.) may emit acoustic waveforms specific to the type of dispenser. The memory 18 may store one or more acoustic waveforms, wherein each acoustic waveform represents a specific type of dispenser. In addition, the memory 18 may be programmable to enable calibration and/or recalibration of the device 12 to adjust to an acoustic waveform emitted by the associated dispenser. The ability to calibrate the device 12 may enable the device to adjust to any changes in an acoustic waveform emitted by the associated waveform (e.g., over a period of time). In addition, the memory 18 may store predefined tolerance thresholds. The processor 20 upon receiving the signal representative of the detected acoustic waveform may compare the signal (i.e., detected acoustic waveform) to the one or more acoustic waveforms stored on the memory 18 to determine the occurrence of the release event. If the detected acoustic waveform matches one of the acoustic waveforms, then the processor 20 determines that a release event occurred. In certain embodiments, the processor 20 may determine a match has occurred if the detected acoustic waveform is within predefined tolerance thresholds of one or more of the stored acoustic waveforms. For example, one or more characteristics (e.g., amplitude, frequency, etc.) of the detected acoustic waveform may need to be within a certain percent (e.g., approximately 5%, 10%, etc.) of a threshold or fall within a given threshold range relative to the respective characteristics one or more of the stored acoustic waveforms. The processor 20 may generate a timestamp of when the release event occurred.

The proximity detection device 24 is configured to detect a location and/or identifier of a caregiver within a proximity of the device 12 or dispenser. For example, the proximity detection device 24 may include a transceiver (e.g., combination transmitter and detector) such as a radio frequency (RF) transceiver (e.g., Bluetooth, ZigBee, UWB, etc.) configured to communicate with a tag (RF tag) worn by the caregiver (e.g., nurse, physician, etc.) within the proximity of the device 12 or dispenser. The proximity detection device 24 may receive a signal from the RF tag that includes a location address and/or identifier (e.g., identifier code or other identifying information) of the caregiver. Alternatively, the proximity detection device 24 may receive a signal from a separate transmitter (i.e., separate from the caregiver) that includes the location address and/or identifier of the caregiver. In some embodiments, the proximity detection 24 may include a voice recognition system to record speech within the proximity of the device or dispenser. The detected speech may be wirelessly transmitted to the server 14 for recognizing the caregiver from the speech and for determining a location address and/or identifier for the caregiver. The processor 20 may generate a timestamp of when the caregiver entered within the proximity of the device 12 or dispenser. In certain embodiments, the processor 20 may generate a timestamp of when the caregiver passed outside of the proximity of the device 12 or dispenser.

Upon detecting the release event when the caregiver is within proximity of the device 12 or dispenser, the processor 20 may associate (i.e., link) the caregiver with the detected release event. The processor 20 may wirelessly communicate data including the association (e.g., occurrence of release event and identifier and/or location address of caregiver) to the server 14 via the wireless interface 26. The processor 20 may also communicate a time when the caregiver was detected within proximity of the device 12 or dispenser and/or a time when the release event occurred to the server 14 via the wireless interface 26. The wireless signal transmitted from the wireless interface 26 including the data described above may be electromagnetic, infrared, optical, or any other type of wireless signal. In certain embodiments, the device 12 may be coupled, via a wired connection, to the server 14 (e.g., via Ethernet or other wired network). The server 14 may receive the data (e.g., data relating to associated caregiver and release event) from the processor 20 to determine whether the occurrence of the release event occurred prior to a predefined event to determine hand hygiene compliance. For example, the caregiver may be given a predefined time frame upon entering the proximity of the device 12 or dispenser to actuate the release event. Also, the caregiver may be given a predefined time frame prior to occurrence of providing treatment or delivery of care or diagnosis to a patient to actuate the release event. The server 14 may be coupled to one or more networks (e.g., hospital information system (HIS)), storage devices, and/or processors separate from the device 12.

The power source 28 to provide electrical power to the device 12 may include a battery (e.g., replaceable or rechargeable). Also, the power source 28 may include a solar charger device to collect solar energy to charge the battery or other storage device. Alternatively, the power source 28 may include a piezoelectric device to collect power for the device 12. In certain embodiments, the power source 28 may include a power plug to couple to an electrical outlet to provide electrical power to the device 12.

One or more of the components of the device 12 (e.g., system on a chip 16, wireless interface 26, transducer 22, proximity detection device 24, and/or power source 28) may be disposed within a single housing 30. An adhesive may be applied to an outer surface of the housing 30 to attach the device 12 on the dispenser or on a surface proximate (e.g., adjacent) to the dispenser, such as at a distance suitable for detecting acoustic events generated at the dispenser. Other means of securing the housing 30 of the device 12 on the dispenser or on a surface proximate to the dispenser may be utilized (e.g., hook and loop fasteners, hooks, etc.). The device 12 enables management of hand hygiene in a simple manner at lower costs to the healthcare facility.

Figure 2:
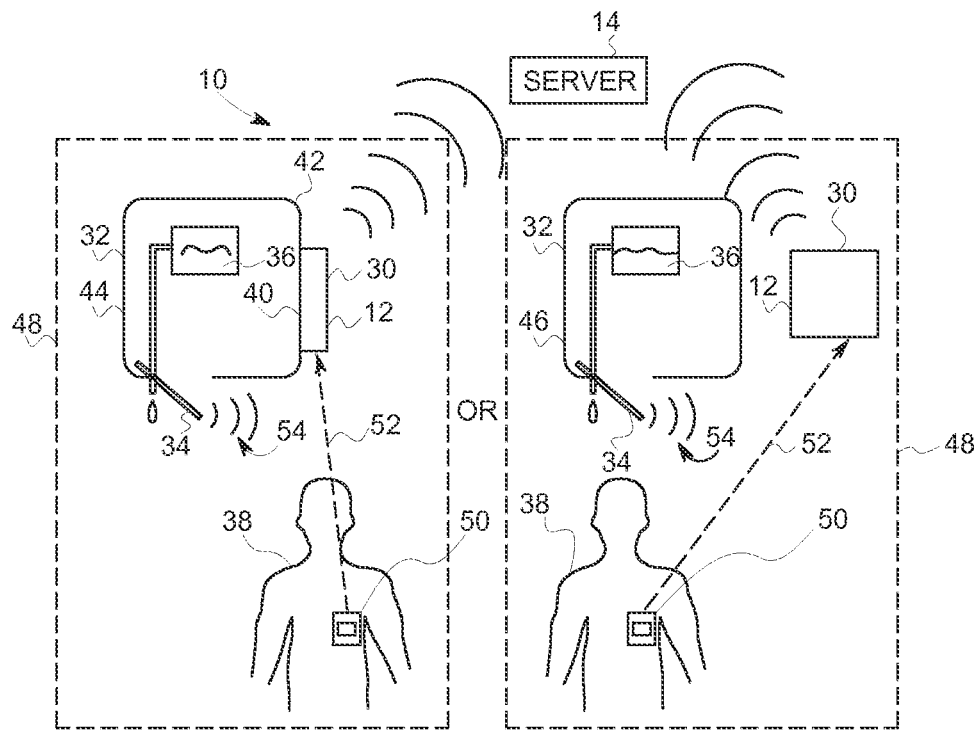
FIG. 2 depicts a diagrammatical representation of an embodiment of the system utilizing the device of FIG. 1.

FIG. 2 depicts a diagrammatical representation of an embodiment of the system 10 utilizing the device 12 of FIG. 1. The system 10 includes one or more dispensers 32. Each dispenser 32 may include an actuator lever or lever arm 34 that when pulled, pressed or otherwise moved causes the release or dispense of a dose of soap or sanitizer 36. For example, a caregiver 38 (e.g., caregiver, doctor, nurse, etc.) may apply a force to move the actuator lever 34 to trigger the release of the soap or sanitizer 36. The type of actuator lever 34, the type of soap or sanitizer 36, and/or the measure of dose of the soap or sanitizer 36 may vary. The dispenser 32 can be motorized or operated manually to pump or release the dose of soap or sanitizer 36. The dispenser 32 can release a dose of soap or sanitizer 36 in a sufficient amount (e.g., multiple shots of predetermined amount (or unit dose size)) upon pressing the lever 34 of the dispenser 32 (e.g., dispense one shot per compression of the actuator lever 34). The dispenser 32 can be refillable and stationary, or issued from and returned to a control station that refills each dispenser 32. Another example of the supply of soap or sanitizer 36 in the dispenser 32 can be provided in replaceable, throwaway, soap or sanitizing agent-containing cartridges of single or multiple storage compartments.

As described above, an outer surface 40 of the device 12 may be attached to an outer surface 42 (e.g., via an adhesive) of the dispenser 32 (e.g., dispenser 44). Alternatively, the device 12 may be attached to a surface proximate to the dispenser 32 (e.g., dispenser 46).

As described above, each device 12 may include the proximity detection device 24 to detect a location and/or identifier of the caregiver 38 within a predetermined proximity 48 of the device 12 or dispenser 32. For example, the proximity detection device 24 may include a transceiver (e.g., combination transmitter and detector) such as a radio frequency (RF) transceiver (e.g., Bluetooth, ZigBee, UWB, etc.) configured to communicate with a tag 50 (RF tag) worn by the caregiver 38 (e.g., nurse, physician, etc.) within the proximity 48 of the device 12 or dispenser 32. The proximity detection device 24 may receive a signal 52 from the RF tag 50 that includes a location address and/or identifier (e.g., identifier code or other identifying information) of the caregiver 38. Alternatively, the proximity detection device 24 may receive a signal from a separate transmitter (i.e., separate from the caregiver 38) that includes the location address and/or identifier of the caregiver 38 derived from the tag 50. The device 12 (e.g., processor 20) may generate a timestamp of when the caregiver 38 entered within the proximity 48 of the device 12 or dispenser 32. In certain embodiments, the device 12 may generate a timestamp of when the caregiver 38 passed outside of the proximity 48 of the device 12 or dispenser 32.

In addition, the device 12 may detect (e.g., via the transducer 22) an acoustic waveform 54 emitted from the dispenser upon the release event of the soap or sanitizer 36. The device 12 upon detecting the acoustic waveform 54 may compare the signal (i.e., detected acoustic waveform 54) to the one or more acoustic waveforms (e.g., stored on the memory 18 of the device 12) to determine the occurrence of the release event. If the detected acoustic waveform 54 matches one of the acoustic waveforms, then the device 12 determines that a release event occurred. The device 12 may generate a timestamp of when the release event occurred.

If the detected release event occurred while the caregiver 38 was within proximity 48 of the device 12 or dispenser 32, the device 12 may associate (i.e., link) the caregiver 38 with the detected release event. In addition, the device 12 may communicate (e.g., wirelessly) data including the association (e.g., occurrence of release event, identifier and/or location address of caregiver 38, a time when the caregiver 38 was detected within proximity 48 of the device 12 or dispenser 32, and/or a time when the release event occurred) to the server 14. The server 14 may receive the data (e.g., data relating to associated caregiver and release event) from the device 12 and determine whether the occurrence of the release event occurred prior to a predefined event to determine hand hygiene compliance.

Figure 3:
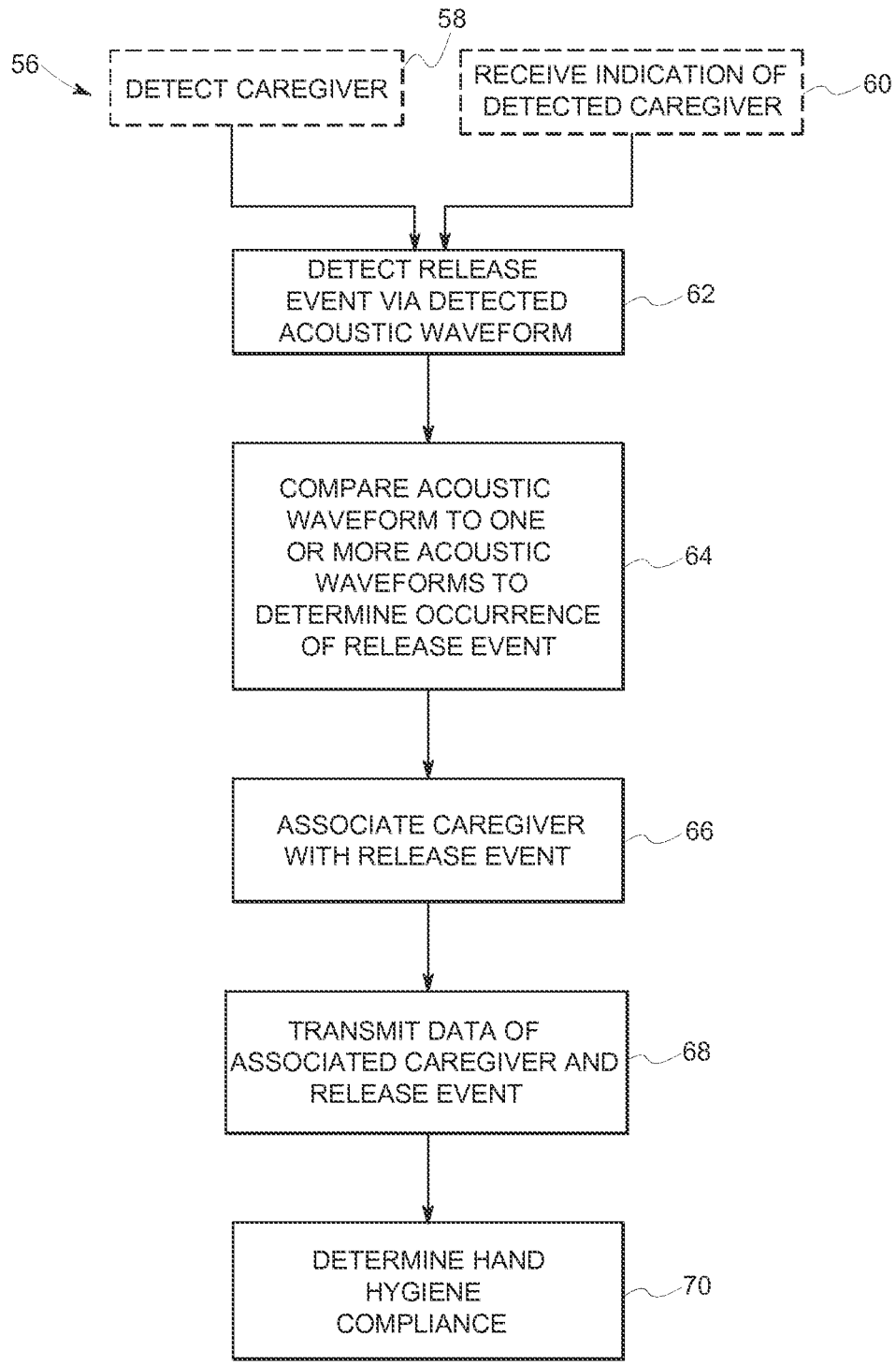
FIG. 3 depicts a flow chart of an embodiment of a method to detect hand hygiene compliance.

FIG. 3 depicts a flow chart of an embodiment of a method 56 to detect hand hygiene compliance utilizing the system 10 of FIGS. 1 and 2. It should be understood that the sequence of acts or steps of the method 56 as discussed in the foregoing description may vary. Also, it should be understood that the method 56 may not require each act or step in the foregoing description, or may include additional acts or steps not disclosed herein. It should also be understood that one or more of the steps of the method 56 can be represented as processor-executable instructions in the memory 18 of the device 12 or other memory associated with the server 14 for execution by one or more processors of the device 12 or other processors associated with the server 14. Also, assume for the sake of example that the system 10 is installed at a healthcare clinic or hospital, and that mobile caregivers 38 (e.g., doctors, nurses, etc.) are provided with wireless tags 50 for communication with the devices 12 (directly or indirectly) disposed in selected areas or rooms of the healthcare facility.

The method 56 may include detecting the caregiver 38, via the proximity detection device 24 of the device 12, when the caregiver 38 is within the proximity 48 of the device 12 or associated dispenser 32 (block 58). For example, the tag 50 of the caregiver 38 may communicate a location address and/or identifier (e.g., identifier code or other identifying information) of the caregiver 38. Alternatively, the method 56 may include receiving an indication of the caregiver 38 being within the proximity 48 of the device 12 or associated dispenser 32 from a separate transmitter (i.e., separate from the caregiver 38) that includes the location address and/or identifier of the caregiver 38 derived from the tag 50 (block 60). The device 12 (e.g., processor 20) may generate a timestamp of when the caregiver 38 entered within the proximity 48 of the device 12 or associated dispenser 32. In certain embodiments, the device 12 may generate a timestamp of when the caregiver 38 passed outside of the proximity 48 of the device 12 or associated dispenser 32.

The method 56 also includes the device 12 detecting a release event via the detected acoustic waveform 54 as described above (block 62). The method 56 further includes the device 12 comparing the detected acoustic waveform 54 to one or more acoustic waveforms (e.g., stored on the memory 18) to determine the occurrence of the release event (block 64). Upon determining the occurrence of the release event while the caregiver 38 is within proximity 48 of the device 12 or associated dispenser 32, the method 56 includes the device 12 associating the caregiver 38 with the release event (block 66). The method 56 yet further includes the device 12 transmitting data of the associated caregiver and release event (e.g., to the server 14) (block 68). As described above, the data may include occurrence of the release event, identifier and/or location address of caregiver 38, a time when the caregiver 38 was detected within proximity 48 of the device 12 or dispenser 32, and/or a time when the release event occurred. The method 56 still further includes (e.g., the server 14) determining hand hygiene compliance based on the data received from the device 12 (block 70). For example, the server 14 may determine whether the occurrence of the release event occurred prior to a predefined event to determine hand hygiene compliance. For example, the caregiver 38 may be given a predefined time frame upon entering the proximity 48 of the device 12 or associated dispenser 32 to actuate the release event. Also, the caregiver 38 may be given a predefined time frame prior to occurrence of providing treatment or delivery of care or diagnosis to a patient to actuate the release event.

Technical effects of the disclosed embodiments include providing the device 12 (e.g., hand hygiene detection device)

to enable detecting hand hygiene compliance. The device 12 may detect the occurrence of a release event of sanitizer or soap from the dispenser 32 associated with the device 12 via the acoustic waveform 54 emitted from the dispenser 32. The device 12 may also detect the caregiver 38 located within the proximity 48 of the device 12 or associated dispenser 32. The device 12 may associate or link the release event with the caregiver 38 being within proximity 48 of the device 12 or associated dispenser 32 during the release event. One or more components of the device 12 may be disposed on the system on a chip 16 within a single housing 30. The device 12 may be disposed directly on or proximate to the dispenser 32. The device 12 may enable management of hand hygiene in a simple manner at lower costs to the healthcare facility.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A device configured to be disposed on or proximate to a dispenser and to detect hand hygiene compliance, comprising:
    a proximity detection device configured to detect a location and an identifier of a caregiver within a proximity of the device;
    a transducer configured to detect a release event from the dispenser by detecting an acoustic waveform emitted from the dispenser when soap or sanitizer is released from the dispenser; and
    a processing device configured to associate the caregiver with the release event based on detecting the acoustic waveform when the caregiver is located within the proximity of the device; and
    a memory configured to store at least one acoustic waveform, wherein the at least one acoustic waveform represents a specific type of dispenser,
    wherein the processing device is configured to receive a signal representative of the detected acoustic waveform from the transducer and to compare the detected acoustic waveform to the at least one acoustic waveform to determine an occurrence of the release event.

2. The device of claim 1, comprising a wireless interface configured to wirelessly transmit data to a server, wherein the data comprises at least the release event and the identifier of the caregiver associated with the release event.

3. The device of claim 2, wherein the data comprises a time when the caregiver was detected within the proximity of the device and a time when the release event occurred.

4. The device of claim 1, wherein the transducer comprises a microphone.

5. The device of claim 1, comprising a system on a chip having the processing device.

6. The device of claim 1, comprising a power source.

7. The device of claim 1, comprising a housing, wherein the proximity detection device, the transducer, and the processing device are disposed within the housing.

8. A device configured to be disposed on or proximate to a dispenser and to detect hand hygiene compliance, comprising:
    a proximity detection device configured to detect a location and an identifier of a caregiver within a proximity of the device;
    a transducer configured to detect a release event from the dispenser by detecting an acoustic waveform emitted from the dispenser when soap or sanitizer is released from the dispenser; and
    a processing device configured to associate the caregiver with the release event based on detecting the acoustic waveform when the caregiver is located within the proximity of the device; and
    a memory, wherein the memory is configured to store a plurality of acoustic waveforms, each acoustic waveform of the plurality of acoustic waveforms representing a different type of dispenser, and wherein the processing device is configured to receive a signal representative of the detected acoustic waveform from the transducer and to compare the detected acoustic waveform to the plurality of acoustic waveforms to determine an occurrence of the release event.

9. The device of claim 8, comprising a housing, wherein the proximity detection device, the transducer, and the processing device are disposed within the housing.

10. The device of claim 8, comprising a wireless interface configured to wirelessly transmit a data to a server, wherein the data comprises at least the release event and the identifier of the caregiver associated with the release event.

11. The device of claim 10, wherein the data comprises a time when the caregiver was detected within the proximity of the device and a time when the release event occurred.

12. A method to detect hand hygiene compliance, comprising:
    detecting, via a proximity detection device, a location and an identifier of a caregiver within a proximity of a dispenser;
    detecting, via a transducer, a release event from the dispenser by detecting an acoustic waveform emitted from the dispenser when soap or sanitizer is released from the dispenser;
    receiving, at a processing device, a signal representative of the detected acoustic waveform from the transducer;
    comparing, via the processing device, the detected acoustic waveform to at least one acoustic waveform stored on a memory to determine an occurrence of the release event, wherein the at least one acoustic waveform represents a specific type of dispenser; and
    associating, via a processing device, the caregiver with the release event based on the detected acoustic waveform when the caregiver is located within the proximity of the dispenser.

13. The method of claim 12, comprising wirelessly transmitting, via a wireless interface, data to a server, wherein the data comprises at least the release event and the identifier of the caregiver associated with the release event.

14. The method of claim 13, wherein the data comprises a time when the caregiver was detected within the proximity of the dispenser and a time when the release event occurred.

15. The method of claim 14, comprising determining whether the occurrence of the release event occurred prior to a predefined event.

16. The method of claim 13, wherein the proximity detection device, the transducer, the processing device, and the wireless interface are disposed with a housing of a single device.

17. The method of claim 16, wherein the single device is disposed on or proximate to the dispenser.

18. The method of claim 12, comprising receiving at the processing device a signal representative of the detected acoustic waveform from the transducer, and comparing, via the processing device, the detected acoustic waveform to a plurality of acoustic waveforms stored on a memory to determine an occurrence of the release event, wherein each acoustic waveform of the plurality of acoustic waveforms represents a different type of dispenser.

19. A device configured to be disposed on or proximate to a dispenser and to detect hand hygiene compliance, comprising:
   a memory structure encoding one or more processor-executable routines, wherein the routines, when executed, cause acts to be performed comprising:
      receiving an identifier of a caregiver within a proximity of the device;
      receiving, from a transducer, a signal representative of a detected acoustic waveform emitted from the dispenser when soap or sanitizer is released from the dispenser during a release event;
      comparing the detected acoustic waveform to at least one acoustic waveform stored on the memory structure to determine an occurrence of the release event, wherein the at least one acoustic waveform represents a specific type of dispenser; and
      associating the caregiver with the release event based on detecting the acoustic waveform when the caregiver is located within the proximity of the dispenser; and
   a processing component configured to access and execute the one or more routines encoded by the memory structure.

20. The device of claim 19, comprising a system on a chip comprising the memory structure and the processing component.

* * * * *